(12) United States Patent
Kubo et al.

(10) Patent No.: US 7,615,656 B2
(45) Date of Patent: Nov. 10, 2009

(54) CYCLOALIPHATIC POLYEPOXY COMPOUNDS AND PREPARATION THEREOF

(75) Inventors: Takashi Kubo, Himeji (JP); Tatsuya Nakano, Himeji (JP); Takahiro Iwahama, Himeji (JP)

(73) Assignee: Daicel Chemical Industries, Ltd., Sakai-shi (JP)

( * ) Notice: Subject to any disclaimer, the term of this patent is extended or adjusted under 35 U.S.C. 154(b) by 0 days.

(21) Appl. No.: 11/819,615

(22) Filed: Jun. 28, 2007

(65) Prior Publication Data

US 2008/0004425 A1   Jan. 3, 2008

(30) Foreign Application Priority Data

Jun. 29, 2006 (JP) .............................. 2006-180449

(51) Int. Cl.
C07D 303/06 (2006.01)
(52) U.S. Cl. ........................ 549/547; 549/531
(58) Field of Classification Search ................ 549/523, 549/531, 547, 533
See application file for complete search history.

(56) References Cited

U.S. PATENT DOCUMENTS

| 5,654,382 A |   | 8/1997 | Dubois et al. |         |
|-------------|---|--------|---------------|---------|
| 5,767,150 A | * | 6/1998 | Fan et al.    | 514/475 |

FOREIGN PATENT DOCUMENTS

| GB | 768157 A    | 2/1957 |
| JP | 02-053850 A | 2/1990 |
| JP | 2005-29632 A| 2/2005 |
| SU | 365356      | 1/1973 |

| WO | WO 2007029448 A1 * | 3/2007 |

OTHER PUBLICATIONS

Chemmical Abstracts WO 2007029448 A1 abstract.*
Database WPI, Derwent Publications Ltd., London, GB; AN 2005-146177 (XP002453984).
Database WPI, Derwent Publications Ltd., London, GB; AN 1990-103245 (XP002453985).
Database WPI, Derwent Publication Ltd., London, GB; AN 1973-59261U (XP002453986).

* cited by examiner

*Primary Examiner*—Bernard Dentz
*Assistant Examiner*—David E Gallis
(74) *Attorney, Agent, or Firm*—Birch, Stewart, Kolasch & Birch, LLP

(57) ABSTRACT

Is disclosed a cycloaliphatic polyepoxy compound represented by following Formula (1):

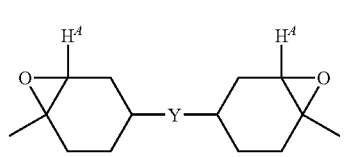

wherein Y represents a linkage group or a single bond; and $H^4$s each represent hydrogen atom at the junction between cyclohexane ring and oxirane ring, and the cyclohexane rings may each further have one or more substituents in addition to the groups shown in the formula. The cycloaliphatic polyepoxy compound contains stereoisomers in such proportions as to have a ratio A/B of 1.8 or more, wherein "A" and "B" are integrated intensities of signals of protons at the junction between cyclohexane ring and oxirane ring as determined by $^1$H-NMR spectroscopy of the compound, in which "A" represents the integrated intensity of a signal observed at a lower magnetic field, and "B" represents the integrated intensity of a signal observed at a higher magnetic field.

9 Claims, No Drawings

CYCLOALIPHATIC POLYEPOXY COMPOUNDS AND PREPARATION THEREOF

BACKGROUND OF THE INVENTION

1. Field of the Invention

The present invention relates to cycloaliphatic polyepoxy compounds and preparation thereof. Such cycloaliphatic polyepoxy compounds are useful typically as energy-ray-curable monomers for use in ultraviolet-curable inks for ink-jet process.

2. Background of the Invention

Ink-jet recording systems have been more and more used, because they are inexpensive, easily produce full-color images, and carry out printing with low noise and high quality. Among them, an ultraviolet-curable ink-jet recording system receives attention, because this system causes less odor and can carry out printing even on recording media that are poor in ink absorption, as compared with solvent-based ink-jet recording systems. Such ultraviolet-curable inks include, for example, radically polymerizable inks and cationically polymerizable inks.

Cationically polymerizable inks do not suffer from polymerization inhibition by the action of oxygen, in contrast to radically polymerizable inks. In addition, they can use light sources with low illuminance and are not so irritative. They, however, produce printed images having quality often varying with temperatures and humidity, and it is difficult to yield high-quality printed images free from feathering or bleeding at high humidity. As a possible solution to these problems, Japanese Unexamined Patent Application Publication (JP-A) No. 2005-29632 discloses an ink composition for ink-jet process which contains a cycloaliphatic polyepoxy compound having a novel structure as an ultraviolet-curable monomer. According to the technique disclosed in the document, the cycloaliphatic polyepoxy compound is synthetically prepared by epoxidation of a corresponding cyclic olefin compound with peracetic acid. However, such cycloaliphatic polyepoxy compounds synthetically prepared using peracetic acid are generally highly viscous, and the resulting inks may not be discharged satisfactorily.

SUMMARY OF THE INVENTION

Accordingly, it is desirable to provide a cycloaliphatic polyepoxy compound having a low viscosity and providing good discharge ability. It is also desirable to provide a process for easily, conveniently, and efficiently prepare a cycloaliphatic polyepoxy compound having these properties.

After intensive investigations, the present inventors found that, by controlling the ratio of stereoisomers of a cycloaliphatic polyepoxy compound, the resulting compound can have a low viscosity and becomes easy to handle, and ultraviolet-curable inks for ink-jet process and other articles can be easily prepared using the cycloaliphatic polyepoxy compound; and that the cycloaliphatic polyepoxy compound can be obtained by oxidizing a corresponding cyclohexene-containing compound with a specific oxidizing agent. The present invention has been made based on these findings.

Specifically, according to an embodiment of the present invention, there is provided a cycloaliphatic polyepoxy compound represented by following Formula (1):

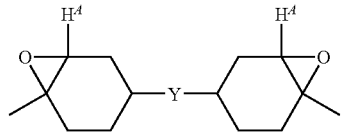

wherein Y represents a linkage group or a single bond; and $H^A$s each represent hydrogen atom at the junction between cyclohexane ring and oxirane ring, and the cyclohexane rings may each further have one or more substituents in addition to the groups shown in the formula. The cycloaliphatic polyepoxy compound contains stereoisomers in such proportions as to have a ratio A/B of 1.8 or more, in which "A" and "B" are integrated intensities of signals of protons at the junction between cyclohexane ring and oxirane ring as determined by $^1$H-NMR spectroscopy of the compound, "A" represents the integrated intensity of a signal observed at a lower magnetic field, and "B" represents the integrated intensity of a signal observed at a higher magnetic field.

Cycloaliphatic polyepoxy compounds represented by Formula (1) include a compound represented by following Formula (1a):

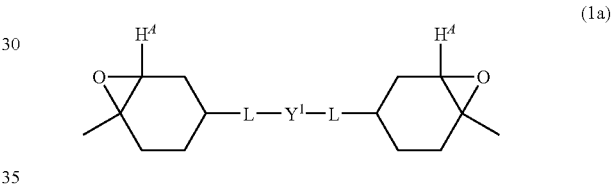

wherein two Ls both represent —C(=O)—O—, where carbonyl group is combined with cyclohexane ring, or two Ls both represent —CH$_2$—O—C(=O)—, where methylene group is combined with cyclohexane ring; $Y^1$ represents a linkage group when the two Ls are both —C(=O)—O—, or $Y^1$ represents a linkage group or a single bond when the two Ls are both —CH$_2$—O—C(=O)—; and $H^A$s each represent hydrogen atom at the junction between cyclohexane ring and oxirane ring, and the cyclohexane rings may each further have one or more substituents in addition to the groups shown in the formula.

According to another embodiment of the present invention, there is provided a process for the preparation of a cycloaliphatic polyepoxy compound represented by following Formula (1):

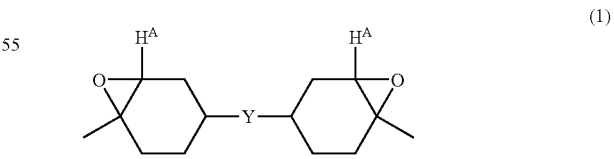

wherein Y represents a linkage group or a single bond; and $H^A$s each represent hydrogen atom at the junction between cyclohexane ring and oxirane ring, and the cyclohexane rings may each further have one or more substituents in addition to the groups shown in the formula. The process includes the step of oxidizing a cyclohexene-containing compound with hydrogen peroxide, in which the cyclohexene-containing compound is represented by following Formula (2):

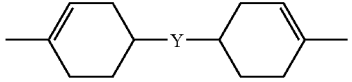

wherein Y is as defined above, and the cyclohexene rings may each further have one or more substituents in addition to the groups shown in the formula.

This process may yield a cycloaliphatic polyepoxy compound represented by Formula (1) which contains stereoisomers in such proportions as to have a ratio A/B of 1.8 or more, in which "A" and "B" are integrated intensities of signals of protons at the junction between cyclohexane ring and oxirane ring as determined by $^1$H-NMR spectroscopy of the compound, "A" represents the integrated intensity of a signal observed at a lower magnetic field, and "B" represents the integrated intensity of a signal observed at a higher magnetic field.

A compound represented by following Formula (1a):

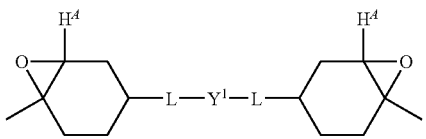

wherein two Ls both represent —C(=O)—O—, where carbonyl group is combined with cyclohexane ring, or two Ls both represent —CH$_2$—O—C(=O)—, where methylene group is combined with cyclohexane ring; $Y^1$ represents a linkage group when the two Ls are both —C(=O)—O—, or $Y^1$ represents a linkage group or a single bond when the two Ls are both —CH$_2$—O—C(=O)—; and H$^4$s each represent hydrogen atom at the junction between cyclohexane ring and oxirane ring, and the cyclohexane rings may each further have one or more substituents in addition to the groups shown in the formula, can be obtained by using, as the cyclohexene-containing compound represented by Formula (2), a compound represented by following Formula (2a):

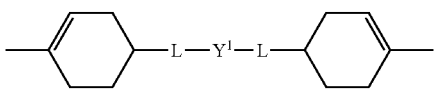

wherein two Ls both represent —C(=O)—O—, where carbonyl group is combined with cyclohexene ring, or two Ls both represent —CH$_2$—O—C(=O)—, where methylene group is combined with cyclohexene ring; $Y^1$ represents a linkage group when the two Ls are both —C(=O)—O—, or $Y^1$ represents a linkage group or a single bond when the two Ls are both —CH$_2$—O—C(=O)—, and the cyclohexene rings may each further have one or more substituents in addition to the groups shown in the formula.

According to another embodiment of the present invention, there is provided a cycloaliphatic polyepoxy compound represented by following Formula (1):

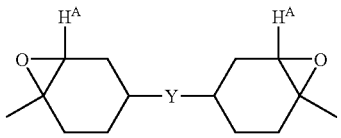

wherein Y represents a linkage group or a single bond; and H$^4$s each represent hydrogen atom at the junction between cyclohexane ring and oxirane ring, and the cyclohexane rings may each further have one or more substituents in addition to the groups shown in the formula, as a product of oxidation of a cyclohexene-containing compound with hydrogen peroxide, in which the cyclohexene-containing compound is represented by following Formula (2):

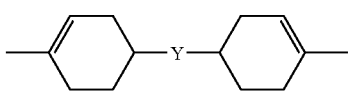

wherein Y represents a linkage group or a single bond, and wherein the cyclohexene rings may each further have one or more substituents in addition to the groups shown in the formula.

The cycloaliphatic polyepoxy compound represented by Formula (1) preferably contains stereoisomers in such proportions as to have a ratio A/B of 1.8 or more, in which "A" and "B" are integrated intensities of signals of protons at the junction between cyclohexane ring and oxirane ring as determined by $^1$H-NMR spectroscopy of the compound, "A" represents the integrated intensity of a signal observed at a lower magnetic field, and "B" represents the integrated intensity of a signal observed at a higher magnetic field.

According to an embodiment of the present invention, there is provided a cycloaliphatic polyepoxy compound which has a low viscosity and, when used typically in an ink for ink-jet process, can be satisfactorily discharged. The cycloaliphatic polyepoxy compound can be used, for example, as an energy-ray-curable monomer for use typically in ultraviolet-curable inks for ink-jet process.

Such a cycloaliphatic polyepoxy compound having these excellent properties can be industrially efficiently prepared by a process according to an embodiment of the present invention.

DESCRIPTION OF THE PREFERRED EMBODIMENTS

A cycloaliphatic polyepoxy compound according to an embodiment of the present invention is represented by Formula (1). In Formula (1), Y represents a linkage group or a single bond. H$^4$s each represent hydrogen atom at the junction between cyclohexane ring and oxirane ring (at the bottom of epoxy group). The cyclohexane rings may each further have one or more substituents in addition to the groups shown in Formula (1).

Examples of the linkage group include substituted or unsubstituted bivalent hydrocarbon groups, substituted or unsubstituted bivalent heterocyclic groups, —O— group, —S— group, —SO— group, —SO$_2$— group, —CO— group, —CS— group, and bivalent groups each containing two or more of these groups combined with each other. Examples of the bivalent hydrocarbon groups include alkylene groups (including alkylidene groups) having about one to about fifteen carbon atoms, such as methylene, ethylidene, isopropylidene, ethylene, 1,2-propanediyl (propylene), 1,3-propanediyl (trimethylene), 2,2-dimethyl-1,3-propanediyl, 1-methyl-1,3-propanediyl, 1,4-butanediyl (tetramethylene), 1,5-pentanediyl (pentamethylene), and 1,6-hexanediyl (hexamethylene) groups, of which those having about one to about ten carbon atoms are preferred; alkenylene groups having about two to about fifteen carbon atoms, such as vinylene group, of which those having about two to about ten carbon atoms are preferred; alkynylene groups having about two to about fifteen carbon atoms, such as ethynylene group, of which those having about two to about ten carbon atoms are preferred; cycloalkylene groups (including cycloalkylidene groups) having about three to about fifteen carbon atoms, such as cyclopentylidene, cyclohexylidene, 1,3-cyclopentanediyl, 1,2-cyclohexanediyl, 1,3-cyclohexanediyl, and 1,4-cyclohexanediyl groups, of which those having about three to about eight carbon atoms are preferred; arylene groups having about six to about fifteen carbon atoms, such as p-phenylene, m-phenylene, and o-phenylene groups; and groups each containing two or more of these groups combined with each other, such as α,α'-o-xylylene group, α,α'-m-xylylene group, α,α'-p-xylylene group, and isopropylidene-bis(p-phenylene) group.

Examples of the bivalent heterocyclic groups include non-aromatic or aromatic bivalent heterocyclic groups each containing at least one hetero atom selected from the group consisting of oxygen atom, sulfur atom, and nitrogen atom, such as 2,5-furandiyl group, 2,5-thiophenediyl group, and 2,5-tetrahydrofurandiyl group, of which those containing at least one hetero atom selected from the group consisting of oxygen atom and sulfur atom are preferred.

The bivalent hydrocarbon groups and the bivalent heterocyclic groups may each have one or more substituents. Examples of such substituents include halogen atoms such as fluorine atom, chlorine atom, and bromine atom; hydroxyl group; alkoxy groups including alkoxy groups having about one to about six carbon atoms, such as methoxy, ethoxy, propoxy, isopropoxy, butoxy, and t-butoxy groups; acyl groups including acyl groups having about one to about ten carbon atoms, such as acetyl, propionyl, and trifluoroacetyl groups; acyloxy groups including acyloxy groups having about one to about ten carbon atoms, such as acetoxy, propionyloxy, and trifluoroacetoxy groups; carboxyl group; alkoxycarbonyl groups including alkoxycarbonyl groups having about two to about ten carbon atoms, such as methoxycarbonyl, ethoxycarbonyl, and t-butoxycarbonyl groups; alkyl groups including alkyl groups having about one to about six carbon atoms, such as methyl, ethyl, isopropyl, butyl, isobutyl, t-butyl, pentyl, and hexyl groups.

Y may contain one or more 3,4-epoxy-4-methyl-cyclohexane-1-yl groups shown in Formula (1).

Specific examples of the linkage group as Y include the examples as the bivalent hydrocarbon groups and the bivalent heterocyclic groups, as well as 2,2-dimethoxy-1,3-propanediyl group, 2,2-bis(methoxymethyl)-1,3-propanediyl group, 2-hydroxy-1,3-propanediyl group, 2-methoxymethyl-2-methyl-1,3-propanediyl group, 2-hydroxymethyl-2-methyl-1,3-propanediyl group, oxydiethylene ($-CH_2CH_2OCH_2CH_2-$) group, thiodiethylene ($-CH_2CH_2SCH_2CH_2-$) group, 3-oxothiodiethylene group, 3,3-dioxothiodiethylene group, 1,4-dimethyl-3-oxa-1,5-pentanediyl group, 3-oxopentanediyl group, 1,5-dioxo-3-oxapentanediyl group, 4-oxa-1,7-heptanediyl group, 3,6-dioxa-1,8-octanediyl group, 1,4,7-trimethyl-3,6-dioxa-1,8-octanediyl group, 5,5-dimethyl-3,7-dioxa-1,9-nonanediyl group, 5,5-dimethoxy-3,7-dioxa-1,9-nonanediyl group, 5,5-bis(methoxymethyl)-3,7-dioxa-1,9-nonanediyl group, 4,7-dioxo-3,8-dioxa-1,10-decanediyl group, 3,8-dioxo-4,7-dioxa-1,10-decanediyl group, furan-2,5-diyl-bis(methylene) group, and thiophene-2,5-diyl-bis(methylene) group.

Y may also be a group represented by following Formula (3) or (4):

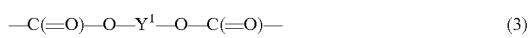

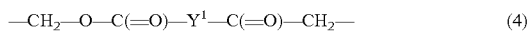

$Y^1$ in Formula (3) represents a linkage group, and $Y^1$ in Formula (4) represents a linkage group or a single bond. The linkage group as $Y^1$ is as with the linkage group as Y.

In Formulae (3) and (4), preferred examples of $Y^1$ include single bond [in Formula (4) alone]; as well as substituted or unsubstituted bivalent hydrocarbon groups having about one to about ten carbon atoms; substituted or unsubstituted bivalent heterocyclic groups; groups each containing two or more of these groups combined with each other; groups each containing any of these bivalent groups combined with one to three groups selected from —O— group, —S— group, —SO— group, —SO$_2$— group, —CO— group, and —CS— group; and groups each containing any of these groups combined with 3,4-epoxy-4-methyl-cyclohex-1-yl group. Specific examples of such groups include ethylene group, 1,3-propanediyl group, 1,2-propanediyl group, 1-methyl-1,3-propanediyl group, 2-methyl-1,3-propanediyl group, 2-hydroxy-1,3-propanediyl group, 2,2-dimethyl-1,3-propanediyl group, 2-methoxymethyl-2-methyl-1,3-propanediyl group, 2-hydroxymethyl-2-methyl-1,3-propanediyl group, 1,4-butanediyl group, oxydiethylene group, thiodiethylene group, 3-oxothiodiethylene group, 3,3-dioxothiodiethylene group, p-phenylene group, furan-2,5-diyl-bis(methylene) group, thiophene-2,5-diyl-bis(methylene) group, 2-(3,4-epoxy-4-methyl-cyclohex-1-ylcarbonyloxy-methyl)-2-methyl-1,3-propanediyl group, and 2,2-bis(3,4-epoxy-4-methyl-cyclohex-1-ylcarbonyloxy-methyl)-1,3-propanediyl group. Among them, typically preferred are alkylene groups having about one to about six carbon atoms, such as methylene group, ethylene group, 1,3-propanediyl group, 1,2-propanediyl group, 1-methyl-1,3-propanediyl group, and 2,2-dimethyl-1,3-propanediyl group.

Examples of substituents which the cyclohexane rings in Formula (1) may have include halogen atoms such as fluorine atom, chlorine atom, and bromine atom; hydroxyl group; alkoxy groups including alkoxy groups having about one to about six carbon atoms, such as methoxy, ethoxy, propoxy, isopropoxy, butoxy, and t-butoxy groups; acyl groups including acyl groups having about one to about ten carbon atoms, such as acetyl, propionyl, and trifluoroacetyl groups; acyloxy groups including acyloxy groups having about one to about ten carbon atoms, such as acetoxy, propionyloxy, and trifluoroacetoxy groups; carboxyl group; alkoxycarbonyl groups including alkoxycarbonyl groups having about two to about ten carbon atoms, such as methoxycarbonyl, ethoxycarbonyl, and t-butoxycarbonyl groups; and alkyl groups including alkyl groups having about one to about six carbon atoms, such as methyl, ethyl, isopropyl, butyl, isobutyl, t-butyl, pentyl, and hexyl groups.

Of cycloaliphatic polyepoxy compounds represented by Formula (1), compounds represented by Formula (1a) are preferred. Such cycloaliphatic polyepoxy compounds of Formula (1a) correspond to compounds of Formula (1) wherein Y is a group represented by Formula (3) or (4).

A cycloaliphatic polyepoxy compound represented by Formula (1) according to an embodiment of the present invention contains stereoisomers in a ratio within a specific range. Specifically, the cycloaliphatic polyepoxy compound contains stereoisomers in such proportions as to have a ratio A/B of 1.8 or more, in which "A" and "B" are integrated intensities of signals of protons at the junction between cyclohexane ring and oxirane ring as determined by $^1$H-NMR spectroscopy of the compound, "A" represents the integrated intensity of a signal observed at a lower magnetic field, and "B" represents the integrated intensity of a signal observed at a higher magnetic field. The signals of the proton are observed at a lower magnetic field and at a higher magnetic field, probably because there are cis- and trans-isomers which are different from each other in steric configuration between Y and the epoxy group combined with the cyclohexane ring.

The ratio A/B is preferably 1.85 or more, and more preferably 1.90 or more. The upper limit of the ratio A/B is not specifically limited, and the higher the ratio A/B is, the better. The upper limit may be, for example, about 50, and preferably about 10, in consideration of controllability. When a cycloaliphatic polyepoxy compound represented by Formula (1) has a ratio A/B of 1.8 or more, the compound may have a satisfactorily low viscosity, and this enables easy preparation of a composition containing the compound, such as an ultraviolet-curable ink for ink-jet process. In contrast, if a compound has a ratio A/B of less than 1.8, the compound may have a high viscosity, and, when used typically in an ink for ink-jet process, the resulting ink may not be discharged satisfactorily.

A cycloaliphatic polyepoxy compound represented by Formula (1) having a ratio A/B of 1.8 or more according to an embodiment of the present invention can be prepared, for example, by oxidizing (epoxidizing) a cyclohexene-containing compound represented by Formula (2) (cyclic olefin compound) with hydrogen peroxide. According to other embodiments of the present invention, there are also provided a process of preparing a cycloaliphatic polyepoxy compound represented by Formula (1) by oxidizing a cyclohexene-containing compound represented by Formula (2) with hydrogen peroxide; and a cycloaliphatic polyepoxy compound represented by Formula (1) prepared by this process. In this connection, a cycloaliphatic polyepoxy compound represented by Formula (1a) can be prepared by using a compound represented by Formula (2a) as the compound represented by Formula (2).

Y in Formula (2) and Y$^1$ in Formula (2a) are as with above. Substituents which the cyclohexene rings in Formulae (2) and (2a) may have are as with the substituents which the cyclohexane rings in Formula (1) may have.

Hydrogen peroxide for use in the reaction is industrially easily available as a 3 to 70 percent by weight aqueous hydrogen peroxide solution. Such a commercially available product can be used as intact or diluted with water. The concentration of the aqueous hydrogen peroxide solution is not specifically limited, but is preferably from 20 to 35 percent by weight from the viewpoints of safety upon handling and economical efficiency.

From the viewpoint of reaction efficiency, the amount of hydrogen peroxide is desirably about 1 to 2 moles and more desirably about 1.1 to 1.8 moles, per 1 mole of double bonds contained in the compound represented by Formula (2).

The reaction may be carried out in the presence of a catalyst. Catalysts generally used in reactions where hydrogen peroxide is used as an oxidizing agent can be used herein, of which those used in reactions where hydrogen peroxide is used as an epoxidizing agent are preferred. Examples of such catalysts include (i) catalysts each containing an onium salt in combination with a tungsten-containing heteropolyacid or a salt thereof, (ii) catalysts each containing an onium salt in combination with a tungsten compound and a phosphoric acid, (iii) methyltrioxorhenium (MTO), and (iv) titanosilicates.

Examples of the tungsten-containing heteropolyacid or a salt thereof in the catalysts (i) include 12-tungstophosphoric acid (phosphotungstic acid), arsenotungstic acid, and salts of these, such as sodium salts, potassium salts, and ammonium salts. The amount of the tungsten-containing heteropolyacid or a salt thereof is, for example, about 0.0001 to about 0.1 mole, and preferably about 0.001 to about 0.05 mole, per 1 mole of double bonds contained in the compound represented by Formula (2).

Examples of the onium salt include quaternary ammonium salts and oxonium salts, of which quaternary ammonium salts are preferred. Examples of such quaternary ammonium salts include tetrahexylammonium chloride, tetraoctylammonium chloride, trioctylmethylammonium chloride trioctylethylammonium chloride, cetylpyridinium chloride, tetrahexylammonium bromide, tetraoctylammonium bromide, trioctylmethylammonium bromide, trioctylethylammonium bromide, cetylpyridinium bromide, tetrahexylammonium iodide, tetraoctylammonium iodide, trioctylmethylammonium iodide, trioctylethylammonium iodide, cetylpyridinium iodide, tetrahexylammonium hydrogen sulfate, tetraoctylammonium hydrogen sulfate, trioctylmethylammonium hydrogen sulfate, trioctylethylammonium hydrogen sulfate, cetylpyridinium hydrogen sulfate, dilauryldimethylammonium chloride, lauryltrimethylammonium bromide, stearyltrimethylammonium chloride, and distearyldimethylammonium bromide. Among them, cetylpyridinium chloride and trioctylmethylammonium chloride are preferred. Each of these onium salts can be used alone or in combination. The amount of the onium salt(s) is, for example, about 0.01 to about 10 moles, and preferably about 0.1 to about 5 moles, per 1 mole of tungsten atom.

Examples of the tungsten compounds in the catalysts (ii) include tungstates such as sodium tungstate, potassium tungstate, and ammonium tungstate; 12-tungstophosphoric acid; and 12-tungstophosphates such as sodium 12-tungstophosphate, potassium 12-tungstophosphate, and ammonium 12-tungstophosphate. Of these, sodium tungstate and 12-tungstophosphoric acid are preferred. The amount of the tungsten compound(s) is, for example, about 0.0001 to about 0.1 mole, and preferably about 0.001 to about 0.05 mole, per 1 mole of double bonds contained in the compound represented by Formula (2).

Examples of the phosphoric acid include phosphoric acid, polyphosphoric acid, pyrophosphoric acid; and phosphates such as potassium phosphate, sodium phosphate, ammonium phosphate, potassium hydrogen phosphate, sodium hydrogen phosphate, and ammonium hydrogen phosphate. The amount of the phosphoric acid(s) is, for example, about 0.1 to about 100 moles, and preferably about 0.1 to about 10 moles, per 1 mole of tungsten atom.

The onium salt in the catalysts (ii) are as with the onium salt in the catalysts (i). The amount of the onium salt(s) is, for example, about 0.01 to about 10 moles, and preferably about 0.1 to about 5 moles, per 1 mole of tungsten atom.

The amount of the catalyst (iii) or (iv) is, for example, about 0.0001 to about 0.1 mole, and preferably about 0.001 to about 0.05 mole, per 1 mole of double bonds contained in the compound represented by Formula (2). These catalysts, if used, may be used in combination with a base such as pyridine or triethylamine. The amount of the base is, for example, about 0.1 to about 200 moles, and preferably about 1 to about 50 moles, per 1 mole of methyltrioxorhenium (MTO) or titanosilicate.

A reaction is generally carried out in the presence of water, in which water and an organic solvent may be used in combination as solvents. The organic solvent is preferably one that can be separated into another layer from water, and examples thereof include halogenated hydrocarbons such as chloroform, methylene chloride, and chlorobenzene; aromatic hydrocarbons such as toluene, xylenes, and ethylbenzene; aliphatic hydrocarbons such as hexane and heptane; cycloaliphatic hydrocarbons such as cyclohexane and methylcyclohexane; and esters such as ethyl acetate and butyl acetate. Of these solvents, halogenated hydrocarbons such as chloroform and methylene chloride, and aromatic hydrocarbons such as toluene and xylenes are preferred typically from the viewpoint of reaction efficiency.

The amount of organic solvent(s) for use in the reaction is, for example, about 1 to about 200 times by weight, and preferably about 1 to about 20 times by weight that of the compound represented by Formula (2), from the viewpoints of reactivity and operability.

A reaction temperature is not specifically limited but is preferably within such a range as to prevent self-decomposition of hydrogen peroxide and to maintain the reaction selectivity at high level. The temperature is, for example, preferably about 0° C. to about 120° C., more preferably about 5° C. to about 80° C., and typically preferably about 10° C. to about 60° C. The reaction can be carried out at atmospheric pressure, under a pressure (under a load), or under a reduced pressure. A reaction atmosphere is not specifically limited, and the reaction can be carried out in an atmosphere of an inert gas such as nitrogen or argon gas or in an air atmosphere.

The reaction may be carried out according to any system such as batch system, semi-batch system, or continuous system. For example, the reaction can be conducted by a process in which an aqueous hydrogen peroxide solution is added dropwise to a mixture containing a compound represented by Formula (2), a catalyst, and an organic solvent. The rate of adding the aqueous hydrogen peroxide solution may be set in consideration of reaction rate and removing rate of reaction heat. In addition, the reaction can also be conducted by a process in which a catalyst and an aqueous hydrogen peroxide solution are added dropwise to a mixture containing a compound represented by Formula (2) and an organic solvent. Thus, a cycloaliphatic polyepoxy compound having a ratio A/B of 1.8 or more can be obtained as a result of epoxidation of a compound represented by Formula (2) with hydrogen peroxide.

A reaction product can be separated and purified according to a procedure such as separation into different layers, washing or rinsing, extraction, distillation, concentration, crystallization, filtration, recrystallization, or column chromatography, or any combination of these procedures. A target compound can be separated and purified, for example, by separating the reaction mixture into different liquid layers, washing the organic layer with water to thereby remove excessive hydrogen peroxide and the catalyst, and carrying out distillation or column chromatography. Prior to the purification, the reaction mixture is preferably subjected to treatment with a reducing agent such as sodium hydrogen sulfite or sodium thiosulfate, and with a base such as sodium carbonate or sodium hydrogen carbonate.

A cycloaliphatic polyepoxy compound prepared by a process according to an embodiment of the present invention has a low viscosity, has excellent functions, and can thereby be advantageously used typically as an energy-ray-curable monomer for ultraviolet-curable inks for ink-jet process.

EXAMPLES

The present invention will be illustrated in further detail with reference to several examples below, which, however, are by no means limitative. $^1$H-NMR assay was conducted using a NMR spectrometer JNM-A500 supplied from JEOL Ltd., and the viscosity was measured at a sample amount of 0.5 ml and a temperature of 35° C.±0.2° C. with an E type (cone-plate) viscometer LVDV-III+cp supplied from Brookfield Engineering Laboratories, Inc.

Example 1

In a 500-ml four-neck reactor equipped with a condenser, a thermometer, and a dropping funnel were placed 200 g of chloroform, 20 g (57.4 mmol) of neopentyl glycol-bis-(4-methyl-3-cyclohexenecarboxylate), 0.49 g (0.003 equivalent, 0.17 mmol) of 12-tungsto(VI)phosphoric acid n-hydrate, and 0.18 g (0.009 equivalent, 0.52 mmol) of cetylpyridinium chloride. To the stirred mixture was added dropwise 19.5 g (3 equivalents, 172.2 mmol) of a 30 percent by weight aqueous hydrogen peroxide solution at temperatures within a range of 10° C. to 25° C. After the completion of dropwise addition, the mixture was aged with stirring at 40° C. for five hours. The aged mixture was separated into two layers, and the chloroform layer was extracted and sequentially washed with an aqueous sodium sulfite solution, an aqueous sodium hydrogen carbonate solution, and a saturated aqueous sodium chloride solution. The washed chloroform layer was concentrated under reduced pressure, purified through silica gel column chromatography, and thereby yielded neopentyl glycol-bis-(4-methyl-3,4-epoxy-cyclohexanecarboxylate) represented by following Formula (4) in a yield of 93%. The product was liquid at ordinary temperature (25° C.) and had a viscosity at 35° C. of 255 cP (0.255 Pa·s). The $^1$H-NMR assay of the product revealed that the product had a ratio A/B of 2.56, wherein "A" and "B" are integrated intensities of signals of protons at the junction between cyclohexane ring and oxirane ring (at the bottom of epoxy group), and wherein "A" represents the integrated intensity of a signal observed at a lower magnetic field (3.06 ppm), and "B" represents the integrated intensity of a signal observed at a higher magnetic field (2.99 ppm).

(4)

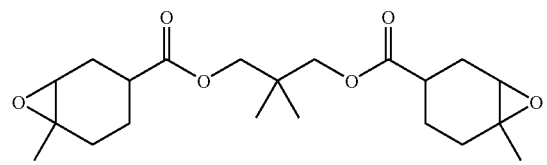

[Spectral Data]
$^1$H-NMR (CDCl$_3$, 500 MHz) δ: 0.96 (s, 3H), 0.97 (s, 3H), 1.31 (s, 3H), 1.32 (s, 3H), 1.44-2.55 (m, 14H), 2.99-3.06 (s, d, 2H), 3.87 (s, 4H)
FT-IR (cm$^{-1}$): 2958-2930, 1727, 1160, 1020, 1004
GC-MS-spectrometry: m/z 380 [electron ionization]

Example 2

In a 500-ml four-neck reactor equipped with a condenser, a thermometer, and a dropping funnel were placed 200 g of toluene, 20 g (57.4 mmol) of neopentyl glycol-bis-(4-methyl-3-cyclohexenecarboxylate), 0.57 g (0.03 equivalent, 1.72 mmol) of sodium tungstate dihydrate, 0.20 g (0.03 equivalent, 1.72 mmol) of a 85 percent by weight aqueous phosphoric acid solution, and 0.23 g (0.01 equivalent, 0.57 mmol) of trioctylmethylammonium chloride (TOMAC). To the stirred mixture was added dropwise 19.5 g (3 equivalents, 172.2 mmol) of a 30 percent by weight aqueous hydrogen peroxide solution at 25° C. After the completion of dropwise addition, the mixture was aged with stirring at 60° C. for five hours. The aged mixture was separated into two layers, the toluene layer was extracted and sequentially washed with an aqueous sodium sulfite solution, an aqueous sodium hydrogen carbonate solution, and a saturated aqueous sodium chloride solution. The washed toluene layer was concentrated under reduced pressure, purified through silica gel column chromatography, and thereby yielded neopentyl glycol-bis-(4-methyl-3,4-epoxy-cyclohexanecarboxylate) represented by Formula (4) in a yield of 82%. The product was liquid at ordinary temperature (25° C.) and had a viscosity at 35° C. of 248 cP (0.248 Pa·s). The $^1$H-NMR assay of the product revealed that the product had a ratio A/B of 2.86, wherein "A" and "B" are integrated intensities of signals of protons at the junction between cyclohexane ring and oxirane ring (at the bottom of epoxy group), and wherein "A" represents the integrated intensity of a signal observed at a lower magnetic field (3.06 ppm), and "B" represents the integrated intensity of a signal observed at a higher magnetic field (2.99 ppm).

Example 3

In a 500-ml four-neck reactor equipped with a condenser, a thermometer, and a dropping funnel were placed 200 g of chloroform, 20 g (57.4 mmol) of neopentyl glycol-bis-(4-methyl-3-cyclohexenecarboxylate), 0.14 g (0.01 equivalent, 0.57 mmol) of methyltrioxorhenium (MTO), and 0.45 g (0.1 equivalent, 5.7 mmol) of pyridine. To the stirred mixture was added dropwise 20 g (3 equivalents, 172.2 mmol) of a 30 percent by weight aqueous hydrogen peroxide solution at temperatures within a range of 10° C. to 25° C. After the completion of dropwise addition, the mixture was aged with stirring at 25° C. for five hours. The aged mixture was separated into two layers, and the chloroform layer was extracted and sequentially washed with an aqueous sodium sulfite solution, an aqueous sodium hydrogen carbonate solution, and a saturated aqueous sodium chloride solution. The washed chloroform layer was concentrated under reduced pressure, purified through silica gel column chromatography, and thereby yielded neopentyl glycol-bis-(4-methyl-3,4-epoxy-cyclohexanecarboxylate) represented by Formula (4) in a yield of 93%. The product was liquid at ordinary temperature (25° C.) and had a viscosity at 35° C. of 241 cP (0.241 Pa·s). The $^1$H-NMR assay of the product revealed that the product had a ratio A/B of 3.33, wherein "A" and "B" are integrated intensities of signals of protons at the junction between cyclohexane ring and oxirane ring (at the bottom of epoxy group), and wherein "A" represents the integrated intensity of a signal observed at a lower magnetic field (3.06 ppm), and "B" represents the integrated intensity of a signal observed at a higher magnetic field (2.99 ppm).

Comparative Example 1

In a 500-ml four-neck reactor equipped with a condenser, a thermometer, and a dropping funnel were placed 200 g of chloroform and 20 g (57.4 mmol) of neopentyl glycol-bis-(4-methyl-3-cyclohexenecarboxylate). To the stirred mixture was added dropwise a solution of 14.8 g (1.5 equivalents, 86.1 mmol) of m-chloroperbenzoic acid in 200 g of chloroform at temperatures within a range of 10° C. to 25° C. After the completion of dropwise addition, the mixture was aged with stirring at 40° C. for three hours. After the aging, precipitated m-chloroperbenzoic acid was removed by filtration, and the filtrate was sequentially washed with an aqueous sodium sulfite solution, an aqueous sodium hydrogen carbonate solution, and a saturated aqueous sodium chloride solution. The washed chloroform layer was concentrated under reduced pressure, purified through silica gel column chromatography, and thereby yielded neopentyl glycol-bis-(4-methyl-3,4-epoxy-cyclohexanecarboxylate) represented by Formula (4) in a yield of 92%. The product was solid (melting point: 35° C.) at ordinary temperature (25° C.) and had a viscosity at 35° C. of 334 cP (0.334 Pa·s). The $^1$H-NMR assay of the product revealed that the product had a ratio A/B of 1.54, wherein "A" and "B" are integrated intensities of signals of protons at the junction between cyclohexane ring and oxirane ring (at the bottom of epoxy group), and wherein "A" represents the integrated intensity of a signal observed at a lower magnetic field (3.06 ppm), and "B" represents the integrated intensity of a signal observed at a higher magnetic field (2.99 ppm).

Comparative Example 2

In a 500-ml four-neck reactor equipped with a condenser, a thermometer, and a dropping funnel were placed 200 g of chloroform and 20 g (57.4 mmol) of neopentyl glycol-bis-(4-methyl-3-cyclohexenecarboxylate). To the stirred mixture was added dropwise 44 g (3 equivalents, 172.2 mmol in terms of peracetic acid) of a 30 percent by weight solution of peracetic acid in ethyl acetate at 40° C. After the completion of dropwise addition, the mixture was aged with stirring at 40° C. for five hours. The aged mixture was diluted with water, separated, and the chloroform layer was extracted and sequentially washed with an aqueous sodium sulfite solution, an aqueous sodium hydrogen carbonate solution, and a saturated aqueous sodium chloride solution. The washed chloroform layer containing ethyl acetate was concentrated under reduced pressure, purified through silica gel column chromatography, and thereby yielded neopentyl glycol-bis-(4-methyl-3,4-epoxy-cyclohexanecarboxylate) represented by Formula (4) in a yield of 90%. The product was solid (melting point: 35° C.) at ordinary temperature (25° C.) and had a viscosity at 35° C. of 319 cP (0.319 Pa·s). The $^1$H-NMR assay of the product revealed that the product had a ratio A/B of 1.69, wherein "A" and "B" are integrated intensities of signals of protons at the junction between cyclohexane ring and oxirane ring (at the bottom of epoxy group), and wherein "A" represents the integrated intensity of a signal observed at a lower magnetic field (3.06 ppm), and "B" represents the integrated intensity of a signal observed at a higher magnetic field (2.99 ppm).

The data of Examples 1 to 3 and Comparative Examples 1 and 2 are shown in Table 1.

TABLE 1

|  | State at Ordinary Temperature | Ratio A/B | Viscosity at 35° C. (Pa·s) |
| --- | --- | --- | --- |
| Example 1 | liquid | 2.56 | 0.255 |
| Example 2 | liquid | 2.86 | 0.248 |
| Example 3 | liquid | 3.33 | 0.241 |
| Comparative Example 1 | solid (melting point: 35° C.) | 1.54 | 0.334 |

TABLE 1-continued

| | State at Ordinary Temperature | Ratio A/B | Viscosity at 35° C. (Pa · s) |
|---|---|---|---|
| Comparative Example 2 | solid (melting point: 35° C.) | 1.69 | 0.319 |

Example 4

In a 500-ml four-neck reactor equipped with a condenser, a thermometer, and a dropping funnel were placed 200 g of chloroform, 20 g (65.3 mmol) of ethylene glycol-bis-(4-methyl-3-cyclohexenecarboxylate), 0.56 g (0.003 equivalent, 0.19 mmol) of 12-tungsto(VI)phosphoric acid n-hydrate, and 0.21 g (0.009 equivalent, 0.59 mmol) of cetylpyridinium chloride. To the stirred mixture was added dropwise 22.2 g (3 equivalents, 195.8 mmol) of a 30 percent by weight aqueous hydrogen peroxide solution at temperatures within a range of 10° C. to 25° C. After the completion of dropwise addition, the mixture was aged with stirring at 40° C. for five hours. The aged mixture was separated, and the chloroform layer was extracted and sequentially washed with an aqueous sodium sulfite solution, an aqueous sodium hydrogen carbonate solution, and a saturated aqueous sodium chloride solution. The washed chloroform layer was concentrated under reduced pressure, purified through silica gel column chromatography, and thereby yielded ethylene glycol-bis-(4-methyl-3,4-epoxy-cyclohexanecarboxylate) represented by following Formula (5) in a yield of 91%. The product was liquid at ordinary temperature (25° C.). The $^1$H-NMR assay of the product revealed that the product had a ratio A/B of 2.15, wherein "A" and "B" are integrated intensities of signals of protons at the junction between cyclohexane ring and oxirane ring (at the bottom of epoxy group), and wherein "A" represents the integrated intensity of a signal observed at a lower magnetic field (3.07 ppm), and "B" represents the integrated intensity of a signal observed at a higher magnetic field (2.99 ppm).

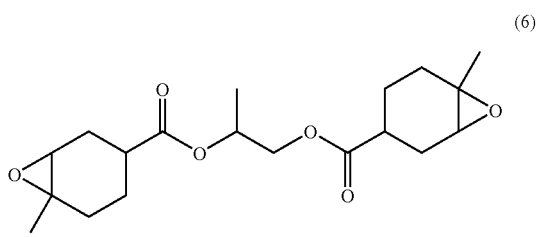

(5)

[Spectral Data]
$^1$H-NMR (CDCl$_3$, 500 MHz) δ: 1.31 (s, 6H), 1.44-2.53 (m, 14H), 2.99-3.07 (s, d, 2H), 4.27 (s, 4H)

Example 5

In a 500-ml four-neck reactor equipped with a condenser, a thermometer, and a dropping funnel were placed 200 g of chloroform, 20 g (62.4 mmol) of propylene glycol-bis-(4-methyl-3-cyclohexenecarboxylate), 0.54 g (0.003 equivalents, 0.19 mmol) of 12-tungsto(VI)phosphoric acid n-hydrate, and 0.20 g (0.009 equivalent, 0.56 mmol) of cetylpyridinium chloride. To the stirred mixture was added dropwise 21.2 g (3 equivalents, 187.2 mmol) of a 30 percent by weight aqueous hydrogen peroxide solution at temperatures within a range of 10° C. to 25° C. After the completion of dropwise addition, the mixture was aged with stirring at 40° C. for five hours. The aged mixture was separated, and the chloroform layer was extracted and sequentially washed with an aqueous sodium sulfite solution, an aqueous sodium hydrogen carbonate solution, and a saturated aqueous sodium chloride solution. The washed chloroform layer was concentrated under reduced pressure, purified through silica gel column chromatography, and thereby yielded propylene glycol-bis-(4-methyl-3,4-epoxy-cyclohexanecarboxylate) represented by following Formula (6) in a yield of 90%. The product was liquid at ordinary temperature (25° C.). The $^1$H-NMR assay of the product revealed that the product had a ratio A/B of 1.92, wherein "A" and "B" are integrated intensities of signals of protons at the junction between cyclohexane ring and oxirane ring (at the bottom of epoxy group), and wherein "A" represents the integrated intensity of a signal observed at a lower magnetic field (3.06 ppm), and "B" represents the integrated intensity of a signal observed at a higher magnetic field (2.99 ppm).

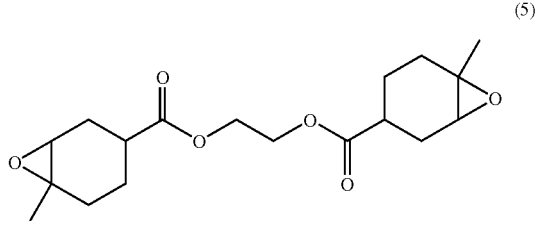

(6)

[Spectral Data]
$^1$H-NMR (CDCl$_3$, 500 MHz) δ: 1.22 (d, 3H), 1.31 (d, 6H), 1.46-2.52 (m, 14H), 2.99-3.06 (s, d, 2H), 3.99-4.04 (m, 1H), 4.16-4.22 (m, 1H), 5.13-5.14 (m, 1H)

Example 6

In a 500-ml four-neck reactor equipped with a condenser, a thermometer, and a dropping funnel were placed 200 g of chloroform, 20 g (62.4 mmol) of succinic acid [bis-(4-methyl-3-cyclohexenylmethyl)]ester, 0.54 g (0.003 equivalent, 0.19 mmol) of 12-tungsto(VI)phosphoric acid n-hydrate, and 0.20 g (0.009 equivalent, 0.56 mmol) of cetylpyridinium chloride. To the stirred mixture was added dropwise 21.2 g (3 equivalents, 187.2 mmol) of a 30 percent by weight aqueous hydrogen peroxide solution at temperatures within a range of 10° C. to 25° C. After the completion of dropwise addition, the mixture was aged with stirring at 40° C. for five hours. The aged mixture was separated, and the chloroform layer was extracted and sequentially washed with an aqueous sodium sulfite solution, an aqueous sodium hydrogen carbonate solution, and a saturated aqueous sodium chloride solution. The chloroform layer was concentrated under reduced pressure, purified through silica gel column chromatography, and thereby yielded succinic acid [bis-(4-methyl-3,4-epoxycyclohex-1-ylmethyl)]ester represented by following Formula (7) in a yield of 92%. The product was liquid at ordinary temperature (25° C.). The $^1$H-NMR assay of the product revealed that the product had a ratio A/B of 1.91, wherein "A" and "B" are integrated intensities of signals of protons at the junction between cyclohexane ring and oxirane ring (at the bottom of epoxy group), and wherein "A" represents the integrated intensity of a signal observed at a lower magnetic field (3.02 ppm), and "B" represents the integrated intensity of a signal observed at a higher magnetic field (2.97 ppm).

(7)

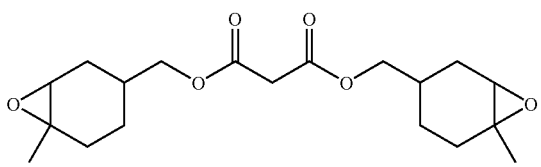

[Spectral Data]
$^1$H-NMR (CDCl$_3$, 500 MHz) δ: 1.31 (d, 6H), 1.41-2.14 (m, 14H), 2.97-3.02 (s, d, 2H), 3.37 (s, 2H), 3.93-4.01 (m, 4H)

While preferred embodiments have been described, it should be understood by those skilled in the art that various modifications, combinations, subcombinations, and alterations may occur depending on design requirements and other factors insofar as they are within the scope or spirit of the appended claims or the equivalents thereof.

What is claimed is:

1. A cycloaliphatic polyepoxy compound represented by following Formula (1):

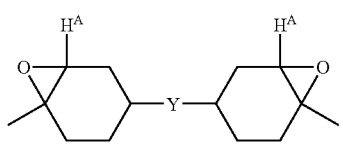

(1)

wherein Y represents a linkage group or a single bond; and H$^4$s each represent hydrogen atom at the junction between cyclohexane ring and oxirane ring, and the cyclohexane rings may each further have one or more substituents in addition to the groups shown in the formula,
wherein the cycloaliphatic polyepoxy compound contains stereoisomers in such proportions as to have a ratio A/B of 1.8 or more, wherein "A" and "B" are integrated intensities of signals of protons at the junction between cyclohexane ring and oxirane ring as determined by $^1$H-NMR spectroscopy of the compound, wherein "A" represents the integrated intensity of a signal observed at a lower magnetic field, and wherein "B" represents the integrated intensity of a signal observed at a higher magnetic field, and
wherein the ratio A/B of 1.8 or more corresponds to a viscosity of 0.31 Pa•s or less at 35° C.

2. The cycloaliphatic polyepoxy compound according to claim 1, wherein the cycloaliphatic polyepoxy compound represented by Formula (1) is a compound represented by following Formula (1a):

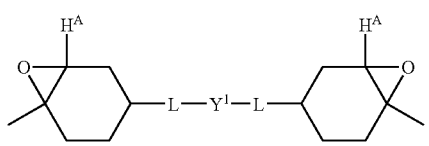

(1a)

wherein two Ls both represent —C(=O)—O—, where carbonyl group is combined with cyclohexane ring, or two Ls both represent —CH$_2$—O—C(=O)—, where methylene group is combined with cyclohexane ring; Y$^1$ represents a linkage group when the two Ls are both —C(=O)—O—, or Y$^1$ represents a linkage group or a single bond when the two Ls are both —CH$_2$—O—C(=O)—; and H$^4$s each represent hydrogen atom at the junction between cyclohexane ring and oxirane ring, and the cyclohexane rings may each further have one or more substituents in addition to the groups shown in the formula.

3. A process for the preparation of a cycloaliphatic polyepoxy compound represented by following Formula (1):

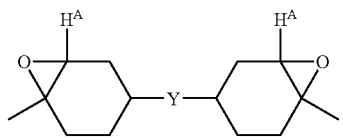

(1)

wherein Y represents a linkage group or a single bond; H$^4$s each represent hydrogen atom at the junction between cyclohexane ring and oxirane ring, and the cyclohexane rings may each further have one or more substituents in addition to the groups shown in the formula, wherein the cycloaliphatic polyepoxy compound represented by Formula (1) contains stereoisomers in such proportions as to have a ratio A/B of 1.8 or more, wherein "A" and "B" are integrated intensities of signals of protons at the junction between cyclohexane ring and oxirane ring as determined by $^1$H-NMR spectroscopy of the compound, wherein "A" represents the integrated intensity of a signal observed at a lower magnetic field, and wherein "B" represents the integrated intensity of a signal observed at a higher magnetic field, and wherein the ratio A/B of 1.8 or more corresponds to a viscosity of 0.31 Pa•s or less at 35° C., the process comprising the step of:

oxidizing a cyclohexene-containing compound with hydrogen peroxide, the cyclohexene-containing compound being represented by following Formula (2):

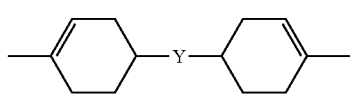

(2)

wherein Y is as defined above; and the cyclohexene rings may each further have one or more substituents in addition to the groups shown in the formula.

4. The process according to claim 3, further comprising using, as the cyclohexene-containing compound represented by Formula (2), a compound represented by following Formula (2a):

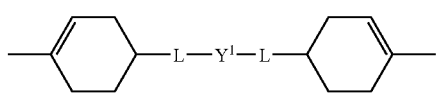

(2a)

wherein two Ls both represent —C(=O)—O—, where carbonyl group is combined with cyclohexene ring, or two Ls both represent —CH$_2$—O—C(=O)—, where methylene group is combined with cyclohexene ring; Y$^1$ represents a linkage group when the two Ls are both —C(=O)—O—, or represents a linkage group or a single bond when the two Ls are both —CH$_2$—O—C(=O)—, and wherein the cyclohexene rings may each further have one or more substituents in addition to the groups shown in the formula, to yield a compound represented by following Formula (1a):

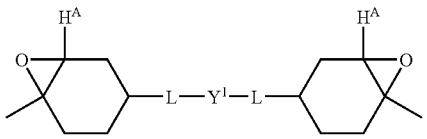

wherein two Ls both represent —C(=O)—O—, where carbonyl group is combined with cyclohexane ring, or two Ls both represent —CH₂—O—C(=O)—, where methylene group is combined with cyclohexane ring; $Y^1$ represents a linkage group when the two Ls are both —C(=O)—O—, or represents a linkage group or a single bond when the two Ls are both —CH₂—O—C(=O)—; and $H^A$s each represent hydrogen atom at the junction between cyclohexane ring and oxirane ring, and the cyclohexane rings may each further have one or more substituents in addition to the groups shown in the formula.

5. A cycloaliphatic polyepoxy compound represented by following Formula (1):

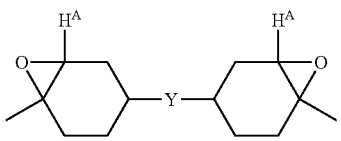

wherein Y represents a linkage group or a single bond; and $H^A$s each represent hydrogen atom at the junction between cyclohexane ring and oxirane ring, and the cyclohexane rings may each further have one or more substituents in addition to the groups shown in the formula, wherein the cycloaliphatic polyepoxy compound represented by Formula (1) contains stereoisomers in such proportions as to have a ratio A/B of 1.8 or more, wherein "A" and "B" are integrated intensities of signals of protons at the junction between cyclohexane ring and oxirane ring as determined by $^1$H-NMR spectroscopy of the compound, wherein "A" represents the integrated intensity of a signal observed at a lower magnetic field, and wherein "B" represents the integrated intensity of a signal observed at a higher magnetic field, and wherein the ratio A/B of 1.8 or more corresponds to a viscosity of 0.31 Pa·s or less at 35° C., as a product of oxidation of a cyclohexene-containing compound with hydrogen peroxide, the cyclohexene-containing compound being represented by following Formula (2):

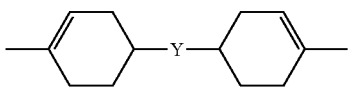

wherein Y is as defined above, and the cyclohexene rings may each further have one or more substituents in addition to the groups shown in the formula.

6. The cycloaliphatic polyepoxy compound according to claim 1, wherein the linkage group of Y is selected from the group consisting of a substituted or unsubstituted bivalent hydrocarbon group, substituted or unsubstituted bivalent heterocyclic group, —O— group, —S— group, —SO— group, —SO₂— group, —CO— group, —CS— group, and a bivalent group each containing two or more of these groups combined with each other.

7. The cycloaliphatic polyepoxy compound according to claim 1, wherein the linkage group of Y is selected from the group consisting of 2,2-dimethoxy-1,3-propanediyl group, 2,2-bis(methoxymethyl)-1,3-propanediyl group, 2-hydroxy-1,3-propanediyl group, 2-methoxymethyl-2-methyl-1,3-propanediyl group, 2-hydroxymethyl-2-methyl-1,3-propanediyl group, oxydiethylene (—CH₂CH₂OCH₂CH₂—) group, thiodiethylene (—CH₂CH₂SCH₂CH₂—) group, 3-oxothiodiethylene group, 3,3-dioxothiodiethylene group, 1,4-dimethyl-3-oxa-1,5-pentanediyl group, 3-oxopentanediyl group, 1,5-dioxo-3-oxapentanediyl group, 4-oxa-1,7-heptanediyl group, 3,6-dioxa-1,8-octanediyl group, 1,4,7-trimethyl-3,6-dioxa-1,8-octanediyl group, 5,5-dimethyl-3,7-dioxa-1,9-nonanediyl group, 5,5-dimethoxy-3,7-dioxa-1,9-nonanediyl group, 5,5-bis(methoxymethyl)-3,7-dioxa-1,9-nonanediyl group, 4,7-dioxo-3,8-dioxa-1,10-decanediyl group, 3,8-dioxo-4,7-dioxa-1,10-decanediyl group, furan-2,5-diyl-bis(methylene) group, and thiophene-2,5-diyl-bis(methylene) group.

8. The cycloaliphatic polyepoxy compound according to claim 2, wherein the linkage group of $Y^1$ is selected from the group consisting of a substituted or unsubstituted bivalent hydrocarbon group, substituted or unsubstituted bivalent heterocyclic group, —O— group, —S— group, —SO— group, —SO₂— group, —CO— group, —CS— group, and a bivalent group each containing two or more of these groups combined with each other.

9. The cycloaliphatic polyepoxy compound according to claim 2, wherein the linkage group of $Y^1$ is selected from the group consisting of 2,2-dimethoxy-1,3-propanediyl group, 2,2-bis(methoxymethyl)-1,3-propanediyl group, 2-hydroxy-1,3-propanediyl group, 2-methoxymethyl-2-methyl-1,3-propanediyl group, 2-hydroxymethyl-2-methyl-1,3-propanediyl group, oxydiethylene (—CH₂CH₂OCH₂CH₂—) group, thiodiethylene (—CH₂CH₂SCH₂CH₂—) group, 3-oxothiodiethylene group, 3,3-dioxothiodiethylene group, 1,4-dimethyl-3-oxa-1,5-pentanediyl group, 3-oxopentanediyl group, 1,5-dioxo-3-oxapentanediyl group, 4-oxa-1,7-heptanediyl group, 3,6-dioxa-1,8-octanediyl group, 1,4,7-trimethyl-3,6-dioxa-1,8-octanediyl group, 5,5-dimethyl-3,7-dioxa-1,9-nonanediyl group, 5,5-dimethoxy-3,7-dioxa-1,9-nonanediyl group, 5,5-bis(methoxymethyl)-3,7-dioxa-1,9-nonanediyl group, 4,7-dioxo-3,8-dioxa-1,10-decanediyl group, 3,8-dioxo-4,7-dioxa-1,10-decanediyl group, furan-2,5-diyl-bis(methylene) group, and thiophene-2,5-diyl-bis(methylene) group.

* * * * *